United States Patent
Rogers et al.

(10) Patent No.: US 10,386,340 B2
(45) Date of Patent: *Aug. 20, 2019

(54) DETECTION OF SUBSTANCES OF INTEREST USING GAS-SOLID PHASE CHEMISTRY

(71) Applicant: Rapiscan Systems, Inc., Torrance, CA (US)

(72) Inventors: William Rogers, Chelmsford, MA (US); Vladimir Romanov, Nashua, NH (US); Stefan Lukow, Hampstead, NH (US); Hartwig Schmidt, Reading, MA (US)

(73) Assignee: Rapiscan Systems, Inc., Torrance, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 15/087,251

(22) Filed: Mar. 31, 2016

(65) Prior Publication Data

US 2017/0284977 A1    Oct. 5, 2017

(51) Int. Cl.
| | |
|---|---|
| *G01N 30/00* | (2006.01) |
| *G01N 30/12* | (2006.01) |
| *G01N 27/62* | (2006.01) |
| *G01N 31/22* | (2006.01) |
| *H01J 49/04* | (2006.01) |
| *H01J 49/00* | (2006.01) |

(52) U.S. Cl.
CPC .......... *G01N 30/12* (2013.01); *G01N 27/622* (2013.01); *G01N 31/224* (2013.01); *H01J 49/0409* (2013.01); *G01N 2030/128* (2013.01); *H01J 49/00* (2013.01)

(58) Field of Classification Search
CPC ............ G01N 30/12; G01N 2030/128; G01N 33/227; G01N 27/622
See application file for complete search history.

(56) References Cited

U.S. PATENT DOCUMENTS

| | | |
|---|---|---|
| 5,491,337 A | 2/1996 | Jenkins |
| 6,211,516 B1 | 4/2001 | Syage |
| 6,326,615 B1 | 12/2001 | Syage |
| 6,329,653 B1 | 12/2001 | Syage |
| 6,630,664 B1 | 10/2003 | Syage |
| 6,642,513 B1 | 11/2003 | Jenkins |

(Continued)

FOREIGN PATENT DOCUMENTS

| | | |
|---|---|---|
| AT | 303589 T | 9/2005 |
| AT | 480769 T | 9/2010 |

(Continued)

OTHER PUBLICATIONS

Ewing et al., "Detection of Volatile Vapors Emitted from Explosives with a Handheld Ion Mobility Spectrometer", Field Analytical Chemistry and Technology, 2001, vol. 5, No. 5, pp. 215-221.

(Continued)

*Primary Examiner* — Blake A Tankersley
(74) *Attorney, Agent, or Firm* — Novel IP

(57) ABSTRACT

The present disclosure is directed to methods and systems for detecting a chemical substance. The methods and systems include using gas-solid phase chemistry to chemically and/or physically modify a substance of interest so that the substance can be vaporized and detected through an analysis of the substance.

22 Claims, 15 Drawing Sheets

(56) References Cited

U.S. PATENT DOCUMENTS

| | | |
|---|---|---|
| 6,690,005 B2 | 2/2004 | Jenkins |
| 6,708,572 B2 | 3/2004 | Jenkins |
| 6,737,642 B2 | 5/2004 | Syage |
| 6,765,198 B2 | 7/2004 | Jenkins |
| 6,815,670 B2 | 11/2004 | Jenkins |
| 6,831,273 B2 | 12/2004 | Jenkins |
| 6,840,122 B1 | 1/2005 | Jenkins |
| 7,047,829 B2 | 5/2006 | Napoli |
| 7,109,476 B2 | 9/2006 | Hanold |
| 7,119,342 B2 | 10/2006 | Syage |
| 7,141,786 B2 | 11/2006 | McGann |
| 7,161,144 B2 | 1/2007 | Syage |
| 7,196,325 B2 | 3/2007 | Syage |
| 7,253,727 B2 | 8/2007 | Jenkins |
| 7,299,710 B2 | 11/2007 | Syage |
| 7,338,638 B2 | 3/2008 | McGann |
| 7,401,498 B2 | 7/2008 | Syage |
| 7,448,248 B2 | 11/2008 | Carey |
| 7,456,393 B2 | 11/2008 | Napoli |
| 7,528,367 B2 | 5/2009 | Haigh |
| 7,541,577 B2 | 6/2009 | Davenport |
| 7,594,422 B2 | 9/2009 | Perry |
| 7,594,447 B2 | 9/2009 | Napoli |
| 7,663,099 B2 | 2/2010 | Reda |
| 7,721,588 B2 | 5/2010 | Perry |
| 7,820,965 B2 | 10/2010 | Nagano et al. |
| 7,856,898 B2 | 12/2010 | Carey |
| 7,880,137 B2 | 2/2011 | McGann |
| 8,161,830 B2 | 4/2012 | Boudries |
| 8,186,234 B2 | 5/2012 | Syage |
| 8,288,735 B2 | 10/2012 | Syage |
| 8,402,842 B2 | 3/2013 | Syage |
| 8,434,375 B1 | 5/2013 | Syage |
| 8,614,582 B2 | 12/2013 | Syage |
| 8,686,355 B2 | 4/2014 | Patterson |
| 8,723,111 B2 | 5/2014 | Syage |
| 8,857,278 B2 | 10/2014 | Syage |
| 8,866,073 B2 | 10/2014 | Goedecke |
| 8,952,327 B2 | 2/2015 | Patterson |
| 9,147,565 B1 | 9/2015 | Goedecke |
| 9,354,153 B2 | 5/2016 | Syage |
| 9,482,655 B2 | 11/2016 | Vilkov |
| 9,528,969 B2 | 12/2016 | Shaw |
| 9,558,924 B2 | 1/2017 | Syage |
| 9,683,981 B1 | 6/2017 | Vilkov |
| 9,689,857 B1 | 6/2017 | Vilkov |
| 9,726,655 B2 | 8/2017 | Syage |
| 9,766,218 B2 | 9/2017 | Lai |
| 9,789,434 B1 | 10/2017 | Lai |
| 2005/0061964 A1 | 3/2005 | Nagano |
| 2008/0230689 A1 | 9/2008 | Stott et al. |
| 2012/0181421 A1 | 7/2012 | Satoh et al. |
| 2014/0030816 A1 | 1/2014 | Gregory et al. |
| 2014/0322518 A1 | 10/2014 | Addleman et al. |
| 2015/0004710 A1 | 1/2015 | Gregory et al. |
| 2015/0010212 A1 | 1/2015 | Segarra |
| 2015/0285780 A1 | 10/2015 | Kelley et al. |
| 2016/0282304 A1 | 9/2016 | Vilkov |
| 2017/0103880 A1 | 4/2017 | Syage |
| 2017/0213715 A1 | 7/2017 | Davila |
| 2017/0261483 A1 | 9/2017 | Vilkov |
| 2017/0261484 A1 | 9/2017 | Vilkov |
| 2017/0284977 A1 | 10/2017 | Rogers |
| 2017/0309463 A1 | 10/2017 | Vilkov |

FOREIGN PATENT DOCUMENTS

| | | |
|---|---|---|
| CA | 2153371 C | 3/1999 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 2436256 C | 6/2007 |
| CN | 2382823 C | 11/2007 |
| CN | 100445767 C | 12/2008 |
| CN | 103308590 A | 9/2013 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| DE | 69528418 T2 | 1/2003 |
| DE | 69926965 T2 | 6/2006 |
| EP | 2368102 A2 | 9/2011 |
| EP | 2637013 A2 | 9/2013 |
| EP | 2778650 A2 | 9/2014 |
| EP | 2778669 A1 | 9/2014 |
| EP | 2884254 A1 | 6/2015 |
| EP | 3015858 A1 | 5/2016 |
| EP | 3032570 A2 | 6/2016 |
| EP | 3040717 A1 | 7/2016 |
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |

OTHER PUBLICATIONS

European Search Report for EP 17 00 0501, dated Jul. 19, 2017, 9 pages.

Sakayanagi et al., "Identification of inorganic anions by gas chromatography/mass spectrometry", Forensic Science International, vol. 157, 2006, pp. 134-143.

DETECTION OF SUBSTANCES OF INTEREST USING GAS-SOLID PHASE CHEMISTRY

BACKGROUND OF THE DISCLOSURE

The embodiments described herein relate generally to a detection technique for chemical substances, and, more particularly, to using reagents to detect contraband substances such as explosives, narcotics, pesticides, and chemical warfare agents by means of spectrometry. More specifically, the methods and systems include using gas-solid phase chemistry to chemically modify a substance of interest so that the substance can be vaporized and detected through an analysis of the substance.

Certain contraband substances—such as inorganic oxidizer salts—are used in formulations for homemade explosives (HMEs). Examples of classes of these explosives include compounds of nitrates, chlorates, perchlorates and permanganates. These compounds have very low volatility, which makes them difficult to detect by detection systems that rely on vaporization of the sample for detection. Examples of these types of detection systems include mass spectrometry (MS) and ion mobility spectrometry (IMS).

As such, in some instances, detection systems are unable to identify potentially dangerous substances because the substance is not able to be vaporized within the detection system. In other instances, substances with a high melting point can only potentially be detected if a desorber is ramped up to high temperatures that produce less than satisfactory limits of detection. Moreover, in such instances, an expensive trap material that can be stable at high temperatures is required and the analysis time is increased (in some instances up to over five times as much time is required).

There remains a need, therefore, for detection systems and methods that chemically modify a substance of interest such that it can be vaporized without increasing analysis time, using extreme temperature ramping and/or using expensive trap materials. The present disclosure achieves these benefits while reducing the exposure of both the user and passenger/cargo to dangerous chemicals and reducing power consumption of the total system.

BRIEF DESCRIPTION OF THE DISCLOSURE

In one embodiment of the present disclosure, a method for detecting a substance of interest is disclosed. The method comprises collecting a sample of a substantially non-volatile substance of interest on a sampling trap; inserting the trap into a thermal desorber; introducing a vaporized clustering agent into the desorber, wherein the clustering agent increases the volatility of the substance of interest; vaporizing the substance of interest; transferring the vaporized substance of interest into a detector; performing an analysis of the substance of interest; and, detecting the substance of interest.

In another embodiment of the present disclosure, a method for detecting a substance of interest is disclosed. The method comprises increasing the volatility of a substantially non-volatile substance of interest, wherein the volatility of the substance of interest is increased by applying a vaporized clustering agent to the substance of interest; vaporizing the substance of interest in a thermal desorber; and, transferring the vaporized substance of interest into a detector, wherein the detector performs an analysis of the vaporized substance of interest and detects the substance of interest.

In another embodiment of the present disclosure, a substance detection system is disclosed. The system comprises a sampling trap including a substantially non-volatile substance of interest; a housing including a clustering agent, the housing configured to vaporize the clustering agent; a thermal desorber configured to receive the sampling trap, wherein the desorber is configured to vaporize the substance of interest; a transfer line, wherein the transfer line connects the housing to the desorber and transfers the vaporized clustering agent from the housing to the desorber, wherein the vaporized clustering agent increases the volatility of the substance of interest; an analysis device coupled in flow communication with the desorber, the analysis device configured to receive the vaporized substance of interest from the desorber and perform an analysis of the substance of interest.

DETAILED DESCRIPTION OF THE DISCLOSURE

Figure 1:
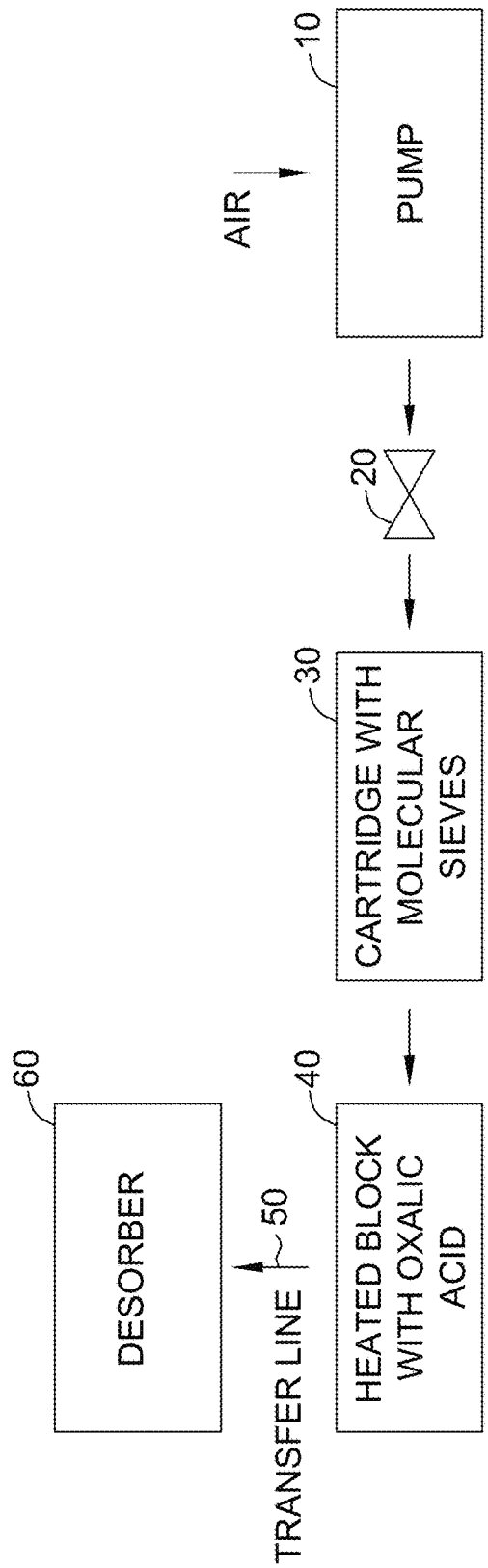
FIG. 1 is an exemplary embodiment of a schematic view of a substance detection system in accordance with the present disclosure.

The embodiments disclosed herein improve detection of substances of interest through the assistance of clustering agents to aid in vaporizing compounds having low and/or no volatility so that the compounds can be detected. Thus, the present disclosure is directed to converting substantially non-volatile substances of interest into a more volatile form so that the substance of interest can be detected through a detection system.

As defined herein, the term "substantially non-volatile" includes both substances that completely lack volatility (i.e., are non-volatile) and substances that have a low volatility, including substances that are not capable of being vaporized in a thermal desorber during the normal use and operating conditions and times of the thermal desorber, such as an ITDX desorber. Volatility is defined as a substance's ability to transform from a solid state to a gaseous state (i.e., vaporized). In some embodiments, a "low volatile" compound includes a compound that is not vaporized at room temperature. In other embodiments, a "low volatile" compound includes a compound that is not vaporized at a temperature of at least about 100° C., at least about 200° C., at least about 300° C., at least about 400° C., at least about 500° C., at least about 600° C. or at least about 700° C. In some embodiments, a "low volatile" compound includes a compound having a vapor pressure of about $10^{-9}$ Torr or below. In other embodiments, a "low volatile" compound includes a compound that has a melting point of at least about 200° C., at least about 240° C., at least about 300° C., at least about 400° C., at least about 500° C., at least about 600° C. or at least about 700° C.

Different substances of interest have different levels of volatility. Substances that are substantially non-volatile are difficult to detect in detection systems because they are not readily transformed from their solid state to their vaporized form, and, as such, the detection systems cannot identify the potentially harmful substance of interest. These substantially non-volatile substances often require extremely high temperatures in order to thermally desorb them. In accordance with the present disclosure, the inventors have surprisingly found a way to convert and detect substantially non-volatile compounds into a more volatile form through the use of gas-solid phase chemistry, wherein the substance of interest begins in a solid state and a clustering agent in the gas phase interacts with the solid substance of interest. The clustering agent chemically and/or physically modifies the substance of interest such that the substance is in a more volatile form and is then vaporized in a thermal desorber and transferred into a detector to be analyzed and detected.

Thus, in one embodiment of the present disclosure, a method for detecting a substance of interest is disclosed. The method comprises collecting a sample of a substantially non-volatile substance of interest on a sampling trap; inserting the trap into a thermal desorber; introducing a vaporized clustering agent into the desorber, wherein the clustering agent increases the volatility of the substance of interest; vaporizing the substance of interest; transferring the vaporized substance of interest into a detector; performing an analysis of the substance of interest; and, detecting the substance of interest.

In another embodiment of the present disclosure, a method for detecting a substance of interest is disclosed, wherein the method comprises increasing the volatility of a substantially non-volatile substance of interest, wherein the volatility of the substance of interest is increased by applying a vaporized clustering agent to the substance of interest; vaporizing the substance of interest in a thermal desorber; and, transferring the vaporized substance of interest into a detector, wherein the detector performs an analysis of the vaporized substance of interest and detects the substance of interest.

The use of the gas-solid phase chemistry to convert the substantially non-volatile substance of interest into a more volatile form is beneficial for use with sampling traps and explosive trace detection devices. The disclosure provides for methods of introducing a clustering agent in the desorber region onto a sampling trap including a substance of interest without having to deposit the clustering agent on the trap. This, in turn, allows for improved control over the amount of clustering agent to be used for the desorption of the substance of interest. Further, the methods disclosed herein do not expose the surface to be swiped to the clustering agent (since the clustering agent is not introduced until the trap is inside the desorber), which also reduces the exposure of the user and/or of the swabbed surface to the dangerous chemicals that may be used. Moreover, the methods disclosed herein reduce the power consumption of the total detection system, since it is not required to ramp the temperature of the desorber to the temperature of the melting point of the substance of interest, which also avoids the use of alternative trap materials. Additionally, the methods disclosed herein provide for a constant amount of clustering agent to be present during each substance of interest analysis, independent of the number of times that the trap has been previously used.

These are significant improvements over previously used methods, as doping a trap material with any amount of clustering agent can potentially cause damage to the surfaces during the harvesting process, since many of the clustering agents used are strong oxidizers or acids and thus even in small amounts are still very reactive compounds. As such, surfaces being swabbed can become discolored and, when humans are being sampled, allergic reactions can occur. The methods and systems of the present disclosure minimize exposure of customers to any dangerous compounds.

In accordance with the present disclosure, in some embodiments, the method includes collecting a sample of a substantially non-volatile substance of interest. In some embodiments, collecting a sample includes using a sampling trap. In some embodiments, the sampling trap is a medium, such as a strip of material that is handled by a user's (e.g., person's) hand or in a wand device. An exemplary method of use is to hold the sampling medium and rub the medium across a surface to collect a sample. In some embodiments, the collected samples include at least one substance of interest. In other embodiments, the collected samples include more than one substance of interest. In some embodiments, the sampling medium includes polytetrafluoroethylene, a paper material and/or derivatives thereof, and combinations thereof. In some embodiments, the sampling trap is used multiple times, which is beneficial for the economy. It should be understood that in some embodiments of the present disclosure, the "sampling trap" is any medium or means known/used in the art for collecting a sample, such as, but not limited to, a trap, a tray, a strip of material, a wand device, an article of clothing, a piece of luggage, a cotton swab, a piece of paper, a glove, a brush and the like.

In some embodiments of the present disclosure, the substantially non-volatile substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant and combinations thereof. In some embodiments, the substance of interest has a melting point of at least about 100° C., at least about 200° C., at least about 240° C., at least about 300° C., or at least about 400° C. In some embodiments, the substance of interest is present on the sampling trap in the solid phase.

In some embodiments, the substantially non-volatile substance of interest includes at least one of an inorganic salt, an organic fuel, an inorganic fuel, and combinations thereof. In some embodiments, the inorganic salt includes at least one of nitrates, chlorates, perchlorates, nitrites, chlorites, permanganates, chromates, dichromates, bromates, iodates, and combinations thereof. In some embodiments, the substance of interest includes at least one of sodium, potassium, ammonium, lithium, strontium, barium, lead, calcium, and combinations thereof. In some embodiments, the substance of interest includes at least one of sodium nitrate, potassium nitrate, strontium nitrate, barium nitrate, sodium chlorate, potassium chlorate, sodium perchlorate, potassium perchlorate, sodium permanganate, potassium permanganate and combinations thereof.

In accordance with the present disclosure, a clustering agent is introduced into the thermal desorber and chemically and/or physically modifies the substantially non-volatile substance of interest, for example, by increasing the volatility of the substance of interest. In some embodiments, the clustering agent is in a non-ionized form. That is, the clustering agent comprises neutral molecules and is in a neutral or uncharged form.

In some embodiments, when the clustering agent comes into contact with the substance of interest, the clustering agent chemically and/or physically modifies the substance of interest by increasing the volatility of the substance of interest. Once the volatility of the substance of interest is increased, the desorber vaporizes the substance of interest and then the substance of interest is transferred into the detector to be analyzed. Thus, whereas in previous industry methods, the substantially non-volatile substance of interest would not be able to be vaporized and transferred into the detector, at least without extreme temperature ramping, which can damage the substance and/or limit the detection thereof, the methods of the present disclosure provide for ways to vaporize the substance of interest through a gas-solid phase interaction.

For example, in some embodiments, a substance of interest is harvested off a suspected surface using a sampling trap (e.g., high performance trap). The swab is then inserted into a heated desorber. Once in the desorber, the swab is exposed to the vaporized clustering agent and heat from the desorber. In some embodiments, non-covalent interaction—such as hydrogen bonds—between the substance of interest in the solid phase with the clustering agent in the gas (i.e., vaporized) phase results in short-lived complexes with binding energies in the order of from about 1 kcal/mol to about 10 kcal/mol. In some embodiments, three processes equally take place in the desorber: (1) coevaporation of the clustering agent with the substance of interest; (2) a chemical modification of the substance of interest through proton exchange reaction between the clustering agent and the substance of interest with the chemically modified substance of interest having a lower melting point and then vaporized within the desorber; or, (3) the clustering agent penetrates into the lattice structure of the substance of interest and lowers the melting point of the substance of interest such that it can be vaporized by the desorber (i.e., melting point lowering by impurity introduction). In some embodiments, the clustering agent forms a non-covalent interaction with the substance of interest. In some embodiments, the clustering agent contributes protons for proton exchange reactions with the substance of interest.

In some embodiments of the present disclosure, the clustering agent includes at least one of an organic acid, a crown ether, an amine, an ester, an amide, and combinations thereof. In some embodiments, the clustering agent includes at least one of oxalic acid, lactic acid, malonic acid, succinic acid, glutaric acid, adipic acid, pimelic acid, and combinations thereof. In some embodiments, the clustering agent includes at least one of an aliphatic compound, an aromatic compound, and combinations thereof.

In some embodiments, the clustering agent includes at least one functional group. In some embodiments, the at least one functional group includes at least one of a carboxyl group, a carbonyl group, an amine group, an ester group, a hydroxyl group, a halogenated alkyl group, a halogenated aromatic group, and combinations thereof. In some embodiments, the clustering agent is a product of thermal decomposition of one or more of the clustering agents described herein.

In accordance with the present disclosure, there are several different ways to introduce the clustering agent into the desorber. In some embodiments, the clustering agent is introduced in a continuous manner. In other embodiments, the clustering agent is introduced in a pulsed manner. When the clustering agent is introduced in a pulsed manner, the agent is introduced at a pulse rate of from about 0.01 Hz to about 10,000 Hz, from about 10 Hz to about 1,000 Hz, or from about 0.01 Hz to about 100 Hz. In some embodiments, the clustering agent is introduced into the desorber simultaneously with or at least about 10 ns, 50 µs, 100 ms, or 5 s after the trap has been inserted into the desorber. In some embodiments, the clustering agent is introduced into the detector at a pulse width of from about 1 second to about 10 seconds, from about 3 seconds to about 7 seconds, or about 5 seconds. In some embodiments, the valve is opening for a time period of from about 0.1 seconds to about 30 seconds.

In some embodiments, the clustering agent is held in a housing, wherein the housing is in flow communication with the thermal desorber through, for example, a transfer line. When the clustering agent is in its vaporized form, it flows from the housing into the desorber. In some embodiments, the housing is in flow communication with a pump, wherein the pump is configured to transfer air into the housing and is configured to transfer the vaporized clustering agent into the desorber. In some embodiments, the pump is in flow communication with a valve. In some embodiments, the pump is in flow communication with a cartridge, wherein the cartridge comprises molecular sieves. In these embodiments, the pump transfers air through the molecular sieves of the cartridge and into the housing, and then also transfers the vaporized clustering agent from the housing into the desorber.

In some embodiments, the clustering agent is placed into the housing in its condensed (i.e., in either solid form, liquid form, or a combination thereof) phase. In some embodiments, the housing includes a permeation tube, wherein the permeation tube includes the clustering agent. The permeation tube is configured to hold the clustering agent in both its condensed and vaporized form.

When the clustering agent is present in the condensed phase in the housing, it needs to be vaporized prior to transferring from the housing to the desorber. In some embodiments, the clustering agent is vaporized through at least one of corona discharge, laser ablation, current-induced desorption, through the use of a heating block, and combinations thereof. Thus, in some embodiments, the housing is a heating block and the clustering agent is located within the heating block. In some embodiments, the temperature within the heating block is from about 45° C. to about 300° C., from about 80° C. to about 150° C., or about 100° C. In some embodiments, the heating block has a constant temperature. In some embodiments, the heating block includes a flash heating mechanism.

Once the clustering agent is vaporized in the housing, the clustering agent is transferred from the housing into the thermal desorber. As noted in this disclosure, the vaporized clustering agent is transferred into the desorber through, for example, a transfer line. In some embodiments, the vaporized clustering agent is introduced (i.e., transferred) from the housing into the desorber at a flow rate of from about 5 cc/min to about 1,000 cc/min, from about 50 cc/min to about 500 cc/min, or from about 100 cc/min to about 250 cc/min. In some embodiments, the vaporized clustering agent is transferred from the housing into the desorber at a concentration rate of from about 0.01 µg/min to about 250 µg/min, from about 10 µg/min to about 150 µg/min, or from about 50 µg/min to about 100 µg/min.

In some embodiments, the method further includes introducing a curtain flow into the desorber, wherein the curtain flow includes at least one of transferring the clustering agent to the desorber and purging an amount of remaining clustering agent from the desorber. In some embodiments, the curtain flow includes dry air. In some embodiments, the dry air is heated, while in other embodiments the dry air is unheated. In some embodiments, the curtain flow is configured to pass through a cartridge comprising molecular sieves. In some embodiments, the curtain flow is operated by a pump, wherein the pump transfers the curtain flow into the desorber. In some embodiments, the curtain flow is transferred through a valve, wherein the valve is selected from the group consisting of a 2-way valve and a 3-way valve. In some embodiments, the curtain flow has a flow rate of from about 50 cc/min to about 200 cc/min, from about 75 cc/min to about 150 cc/min, or about 100 cc/min.

Thus, in some embodiments, the curtain flow functions as a purging mechanism to remove any remaining clustering agent, contaminant, and/or sample from the desorber. That is, once a desired amount of the vaporized substance of interest has been transferred from the desorber into the detector, it is desirable to remove the remaining clustering agent from the desorber prior to the introduction of the next substance of interest from, for example, a sampling trap. In some embodiments, the curtain flow functions to transfer the vaporized clustering agent from the housing into the desorber, from the desorber into the detector, or both.

In some embodiments, after the vaporized substance of interest is transferred into the detector, the detector performs an analysis of the substance of interest, and detects the presence of the substance of interest. In some embodiments, the detector of the present disclosure includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a Raman spectrometer, a laser diode detector, a mass spectrometer (MS), a gas chromatograph (GC), an electron capture detector, a photoionization detector, a chemiluminescence-based detector, an electrochemical sensor, an infrared spectrometer, a lab-on-a-chip detector and combinations thereof.

Detection Systems

In one embodiment of the present disclosure, a substance detection system is disclosed. The system comprises a sampling trap including a substantially non-volatile substance of interest; a housing including a clustering agent, the housing configured to vaporize the clustering agent; a thermal desorber configured to receive the sampling trap, wherein the desorber is configured to vaporize the substance of interest; a transfer line, wherein the transfer line connects the housing to the desorber and transfers the vaporized clustering agent from the housing to the desorber, wherein the vaporized clustering agent increases the volatility of the substance of interest; an analysis device coupled in flow communication with the desorber, the analysis device configured to receive the vaporized substance of interest from the desorber and perform an analysis of the substance of interest.

FIG. 1 discloses an exemplary embodiment of a method and substance detection system in accordance with the present disclosure. In FIG. 1, a pump 10 transfers air through a valve 20 and a cartridge 30 comprising molecular sieves. The air travels through the cartridge 30 and into a housing that includes the clustering agent. In FIG. 1, the housing is a heating block 40 including oxalic acid as the clustering agent. The heating block 40 vaporizes the oxalic acid and then the oxalic acid is transferred from the heating block 40 into the thermal desorber 60 via a transfer line 50. In some embodiments, the pump 10 facilitates the transfer from the heating block 40 into the desorber 60. Once the vaporized clustering agent is transferred into the desorber 60, the vaporized agent interacts with and chemically and/or physically modifies the substance of interest to facilitate the vaporization of the substance within the desorber 60.

Figure 2:
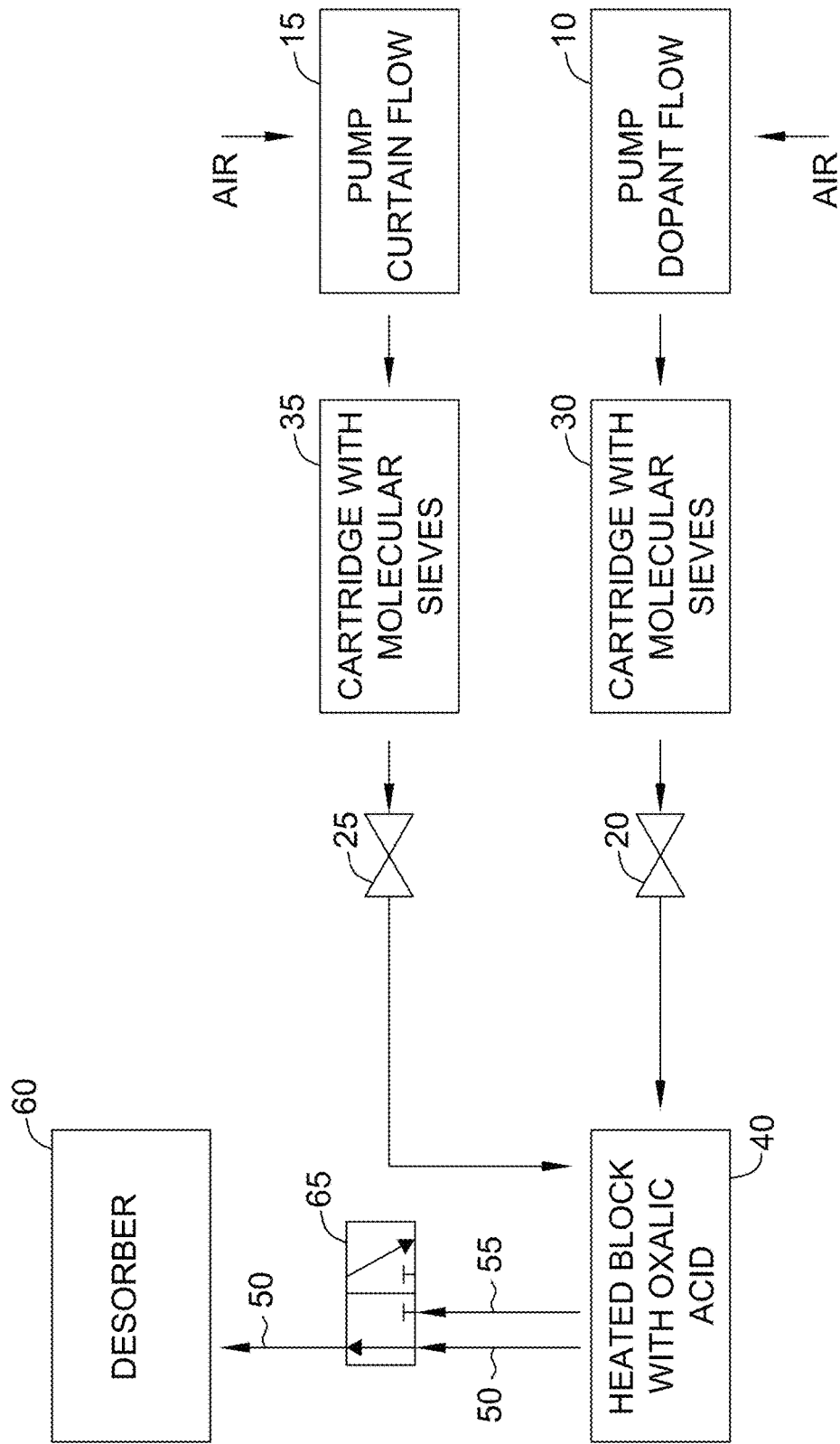
FIG. 2 is an exemplary embodiment of a schematic view of a substance detection system in accordance with the present disclosure.

FIG. 2 discloses another exemplary embodiment of a method and substance detection system in accordance with the present disclosure. In this embodiment, the pump 10 is configured to transfer the clustering agent ("dopant") from the housing (heating block 40) into the desorber 60. Additionally, a curtain flow pump 15 is used to facilitate the transfer of the clustering agent from the heating block 40 into the desorber 60 and is also used to purge the desorber 60 of any remaining clustering agent located therein. The curtain flow travels through a cartridge 35 comprising molecular sieves and a valve 25 before it reaches the heating block 40. The curtain flow then travels from the heating block 40 along a transfer line 55, through a three-way solenoid valve 65. The solenoid valve 65 is configured to switch between transfer lines of the curtain gas—one with and one without the clustering agent.

Figure 3:
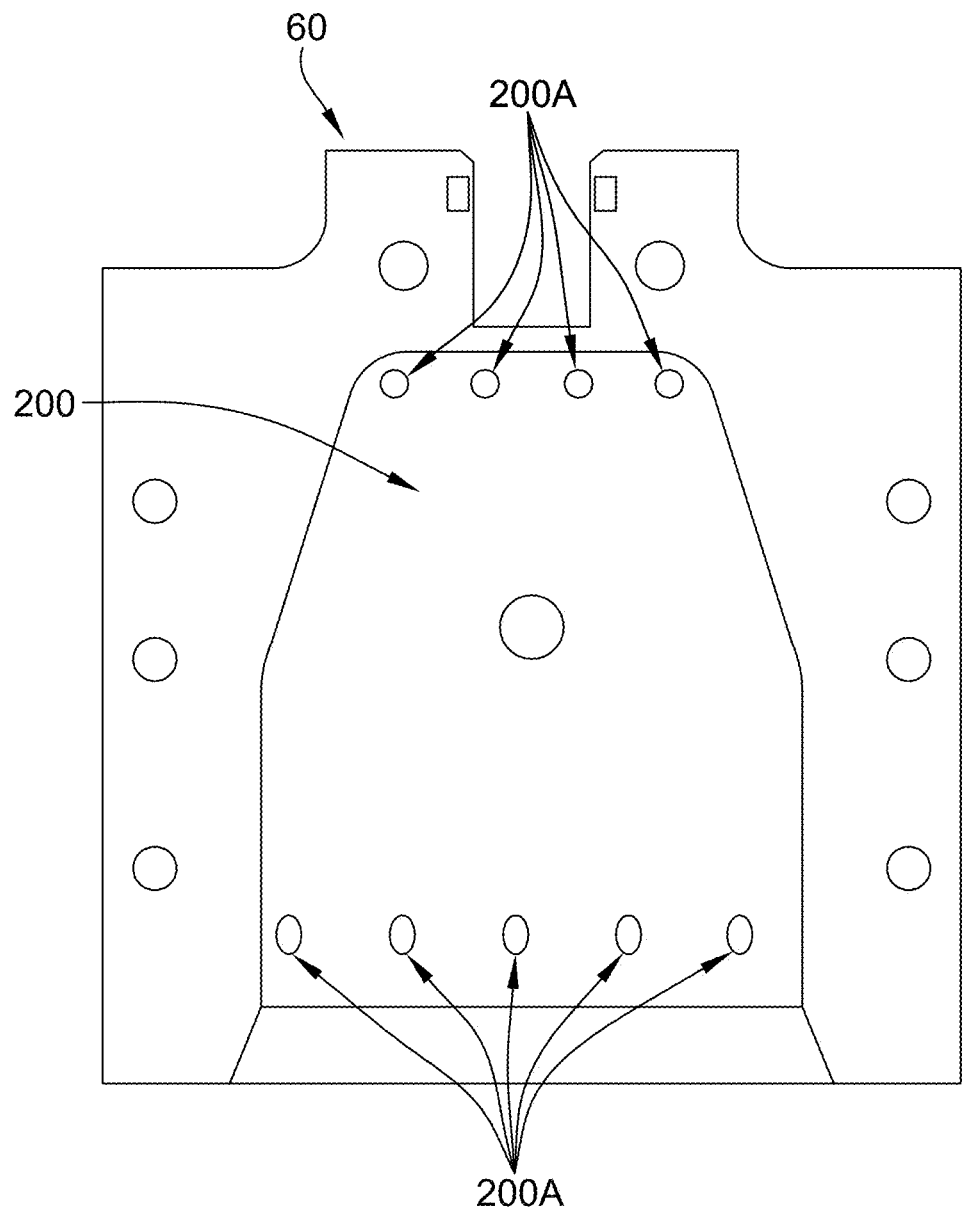
FIG. 3 is an exemplary embodiment of a plate of a thermal desorber in accordance with the present disclosure.

FIG. 3 is an exemplary embodiment of a desorber 60 including a desorber plate 200. In some embodiments, the clustering agent flows through at least one hole 200A in the desorber plate 200.

Figure 14:
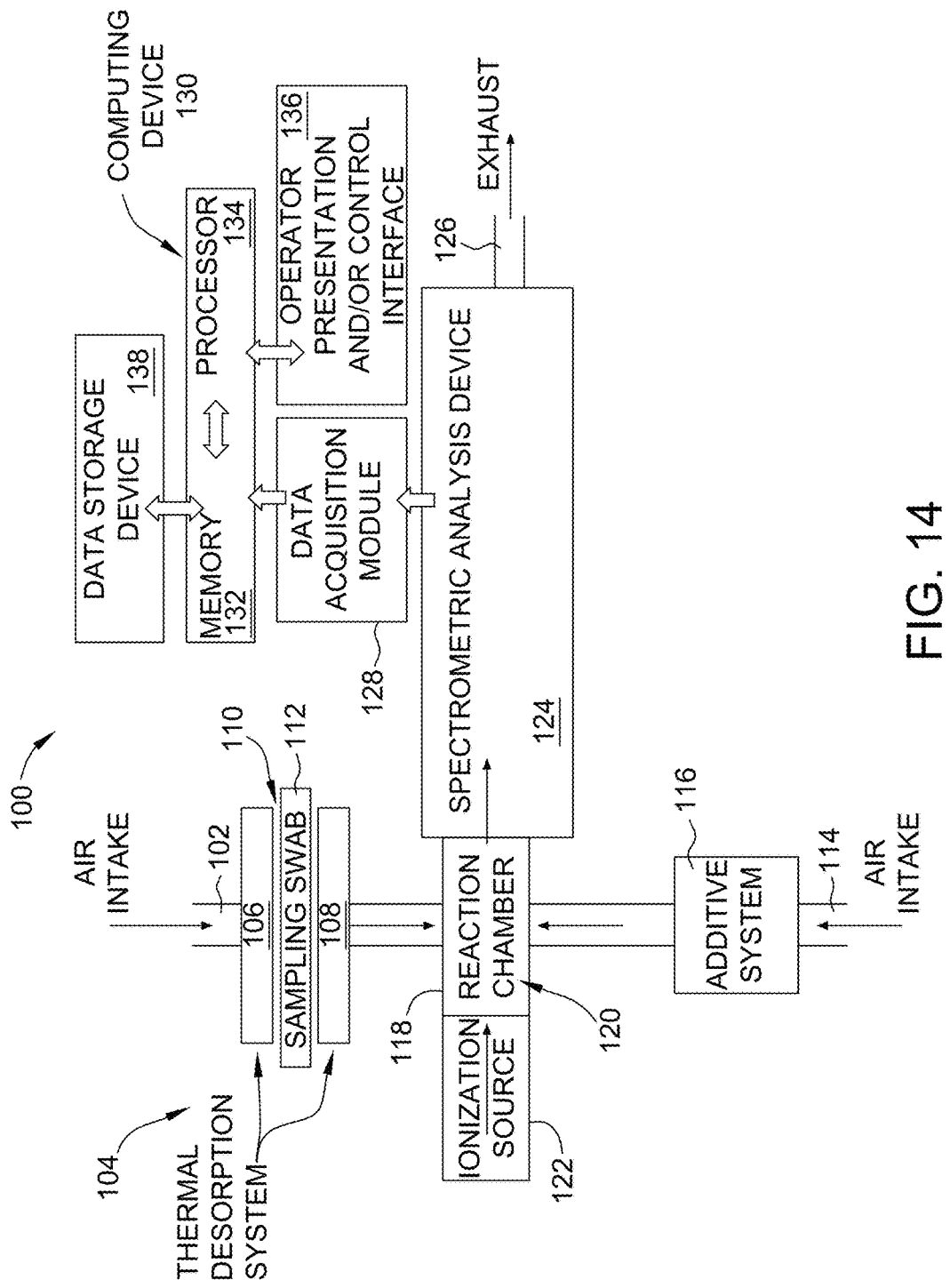
FIG. 14 is an exemplary schematic view of a substance detection system in accordance with the present disclosure.

FIG. 14 is a schematic view of an exemplary substance detection system 100 in accordance with the present disclosure. In the exemplary embodiment, system 100 includes a first air intake device 102. System 100 also includes a sample supply system, i.e., such as a thermal desorption system 104 coupled in flow communication with first air intake device 102. Thermal desorption system 104 further includes a first heating device 106 and a second heating device 108 that define a sampling trap insertion port 110 that receives a sampling trap 112. Alternatively, any configuration of the thermal desorption system 104 that enables operation of system 100 as described herein can be used. In the exemplary embodiment, substance detection system 100 further includes a second air intake device 114 and a reagent (e.g., additive) system 116 coupled in flow communication with second air intake device 114. System 100 further includes a reaction chamber housing 118 defining a reaction chamber 120 coupled in flow communication with thermal desorption system 104 and reagent system 116.

In the exemplary embodiment, system 100 also includes an ionization source 122 coupled in flow communication with reaction chamber 120. Ionization source 122 can be any ionization system that enables operation of system 100 as described herein. Substance detection system 100 further includes a spectrometric analysis device 124 coupled in flow communication with reaction chamber 120. In the exemplary embodiment, spectrometric analysis device 124 is a single quadrupole mass spectrometry device. In alternative embodiments, spectrometric analysis device 124 is any spectrometric analysis system that enables operation of system 100 as described herein, including, without limitation, any mass spectrometry device, any ion mobility spectrometry device, and any differential ion mobility spectrometry device. System 100, in the exemplary embodiment, also includes an exhaust device 126 coupled in flow communication with the spectrometric analysis device 124.

In the exemplary embodiment, substance detection system 100 also includes a data acquisition module 128 coupled to spectrometric analysis device 124. System 100 further includes a computing device 130 coupled to data acquisition module 128. Computing device 130 performs spectrometric analyses of the spectrum data imported from data acquisition module 128. In alternative embodiments, computing device 130 also facilitates control of spectrometric analysis device 124, data acquisition module 128, and any other apparatus associated with substance detection system 100.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

In one embodiment, computing device 130 includes a memory device 132 and a processor 134 operatively coupled to the memory device 132 for executing instructions. In some embodiments, executable instructions are stored in the memory device 132. Computing device 130 is configurable to perform one or more operations described herein by the programming processor 134. For example, processor 134 may be programmed by encoding an operation as one or more executable instructions and providing the executable instructions in memory device 132. In the exemplary embodiment, memory device 132 is one or more devices that enable storage and retrieval of information such as executable instructions and/or other data. Memory device 132 may include one or more computer readable media.

Memory device 132 may be configured to store operational measurements including, without limitation, real-time and historical spectrometric data including, without limitation, sample identification using comparative spectrometric data, isotopic ratios of molecular adduct ions and fragment adduct ions, timing data of elution profiles, thermal desorption profiles, and chromatographic elution profiles for isotopes of adduct ions, and data on ratios of isotopic adduct ions, e.g., relative intensities of isotopic peaks and peak areas of adduct ions in a spectrum, and/or any other type data.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

In the exemplary embodiment, computing device 130, including memory device 132, includes, without limitation, sufficient computer-readable/executable instructions, sufficient data and data structures, algorithms, and commands to facilitate generating comparisons of the data imported from data acquisition module 128 with the stored historical spectrometric data described above. In addition, computing device 130 can either include, or is coupled to, a data storage device 138 that is configured to store such computer-readable/executable instructions, historical data and data structures, algorithms, and commands.

In the exemplary embodiment, substance detection system 100 further includes an operator presentation and/or control interface 136 coupled to computing device 130. Interface 136 presents data, such as spectrometric comparison data to a user (not shown). In some embodiments, interface 136 includes one or more display devices. In some embodiments, interface 136 presents an audible and/or graphical notification upon detection of a substance of interest. Also, in some embodiments, interface 136 facilitates control of computing device 130 and manual data input into computing device 130. Furthermore, in some embodiments, computing device 130 is coupled in communication with one or more other devices, such as another computing device 130, locally or remotely. As such, substance detection system 100 may be networked with other systems and devices such that data transmitted across portions of system 100 may be accessed by any device capable of accessing computing device 130 including, without limitation, desktop computers, laptop computers, and personal digital assistants (PDAs) (neither shown).

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1

Figure 4:
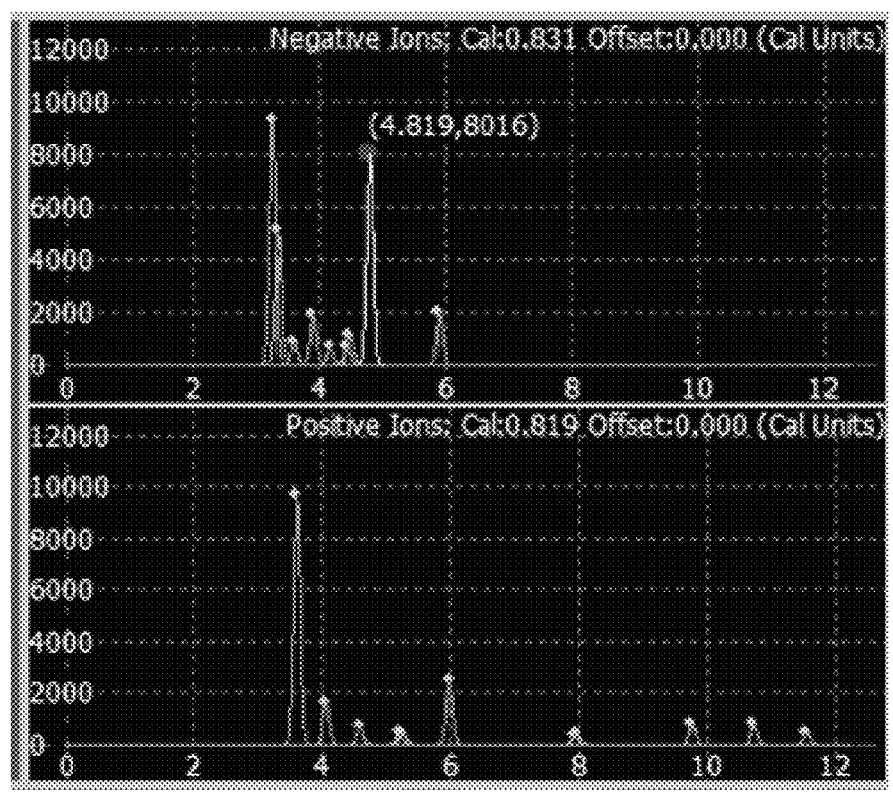
FIG. 4 is an exemplary graph of a blank trap depicting a clustering agent in accordance with the present disclosure.

Example 1 is an exemplary embodiment of the conversion of a substantially non-volatile substance of interest into a more volatile form. Specifically, FIG. 4 depicts the ion mobility spectrum from a sampling medium that included a blank trap and oxalic acid as a clustering agent in accordance with the present disclosure. As shown in FIG. 4, the oxalic acid is present at a peak position of about 4.8 calibrated units.

Figure 5A:
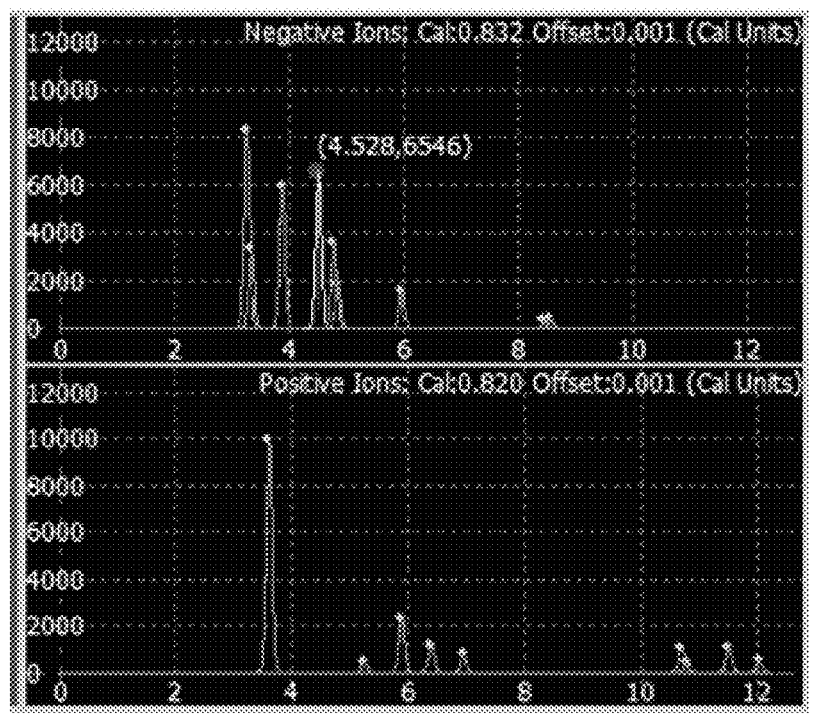
FIG. 5A is an exemplary graph depicting the ion mobility spectrum from a sampling medium including a substance of interest with a clustering agent in accordance with the present disclosure.
Figure 5B:
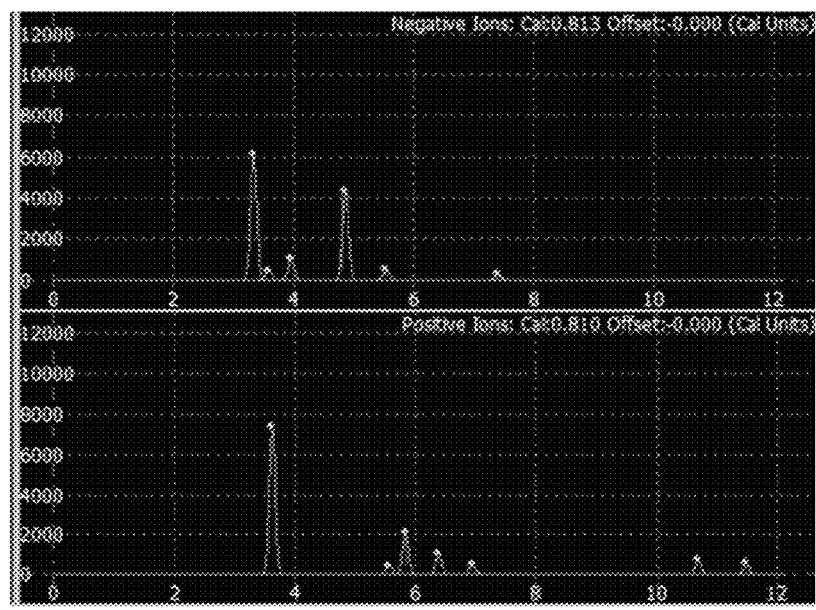
FIG. 5B is an exemplary graph depicting the ion mobility spectrum from a sampling medium including the substance of interest with no clustering agent added in accordance with the present disclosure.

Both FIGS. 5A and 5B depict the ion mobility spectrum from a sampling medium that included sodium nitrate on the sampling trap. FIG. 5B depicts the ion mobility spectrum when no clustering agent was added to the desorber. As shown in FIG. 5B, the detector was unable to detect the presence of sodium nitrate. Comparatively, FIG. 5A depicts the ion mobility spectrum when oxalic acid was introduced in vaporized form as a clustering agent in the desorber, chemically and/or physically modified the sodium nitrate, and then the sodium nitrate was vaporized and transferred into the detector. As shown in FIG. 5A, the detector is able to respond to the presence of sodium nitrate (peak position of about 4.5 calibrated units) due to the sodium nitrate being vaporized after interaction with the oxalic acid and then transferred into the detector from the desorber.

Thus, as shown in Example 1, when the vaporized oxalic acid was introduced into the desorber and interacted with the sodium nitrate, the sodium nitrate was modified such that the desorber vaporized the sodium nitrate and then ultimately transferred the vaporized sodium nitrate into the detector for detection.

Example 2

Figure 6:
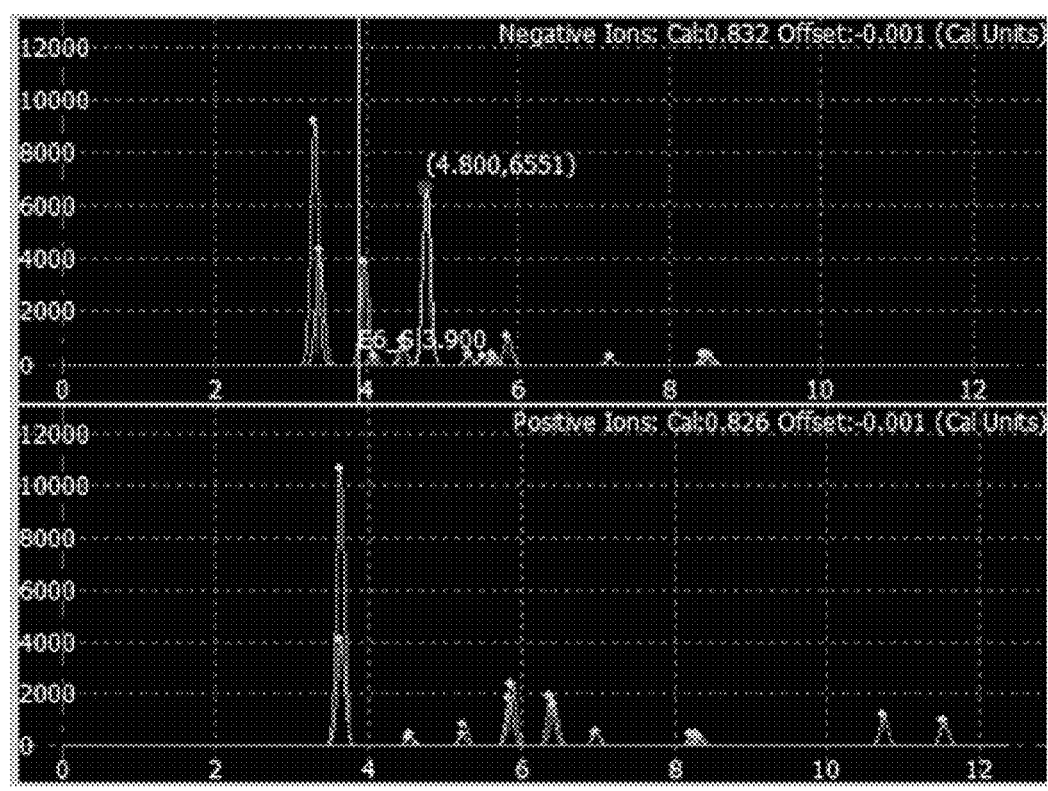
FIG. 6 is an exemplary graph depicting the ion mobility spectrum from a sampling medium including a substance of interest with a clustering agent in accordance with the present disclosure.

Example 2 is an exemplary embodiment of the conversion of a substantially non-volatile substance of interest into a more volatile form. FIG. 6 depicts an ion mobility spectrum when sodium nitrate was present on the sampling trap and oxalic acid was once again used as the clustering agent. As seen in FIG. 6, the sodium nitrate was detected after the interaction with the oxalic acid. As further shown in FIG. 6, however, the peak of sodium nitrate disappeared as the oxalic acid was continued to be entered into the desorber.

Thus, Example 2 shows that if too much clustering agent is supplied to the desorber, eventually the signal of the sodium nitrate is suppressed. Thus, it is important in some embodiments to introduce the clustering agent in a pulsed manner or in a continuous manner at a lower rate so as to not suppress the signal of the substance of interest.

Example 3

Figure 7:
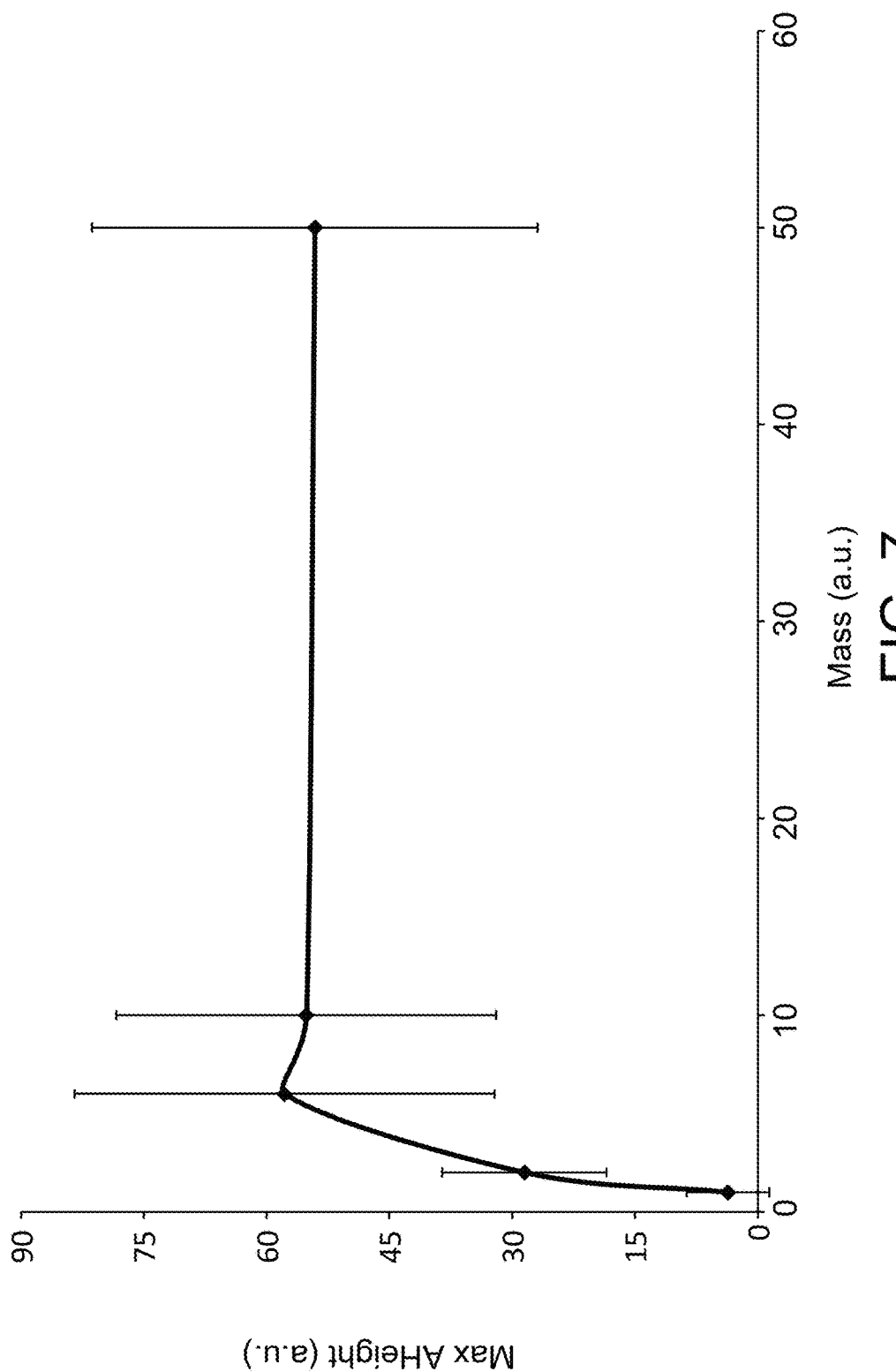
FIG. 7 is an exemplary graph comparing a constant flow of clustering agent and an increase in the amount of a substance of interest in accordance with the present disclosure.

Example 3 is an exemplary embodiment of the effect of a constant amount of clustering agent (oxalic acid) and varying amounts of a substance of interest (sodium nitrate). Specifically, as shown in FIG. 7, the detector provided increased responses as the amount of sodium nitrate was increased. Thus, Example 3 shows that introduction of oxalic acid in a constant manner led to the detection of increased responses for sodium nitrate when the flow rate of the oxalic acid was at a proper rate.

Example 4

Figure 8:
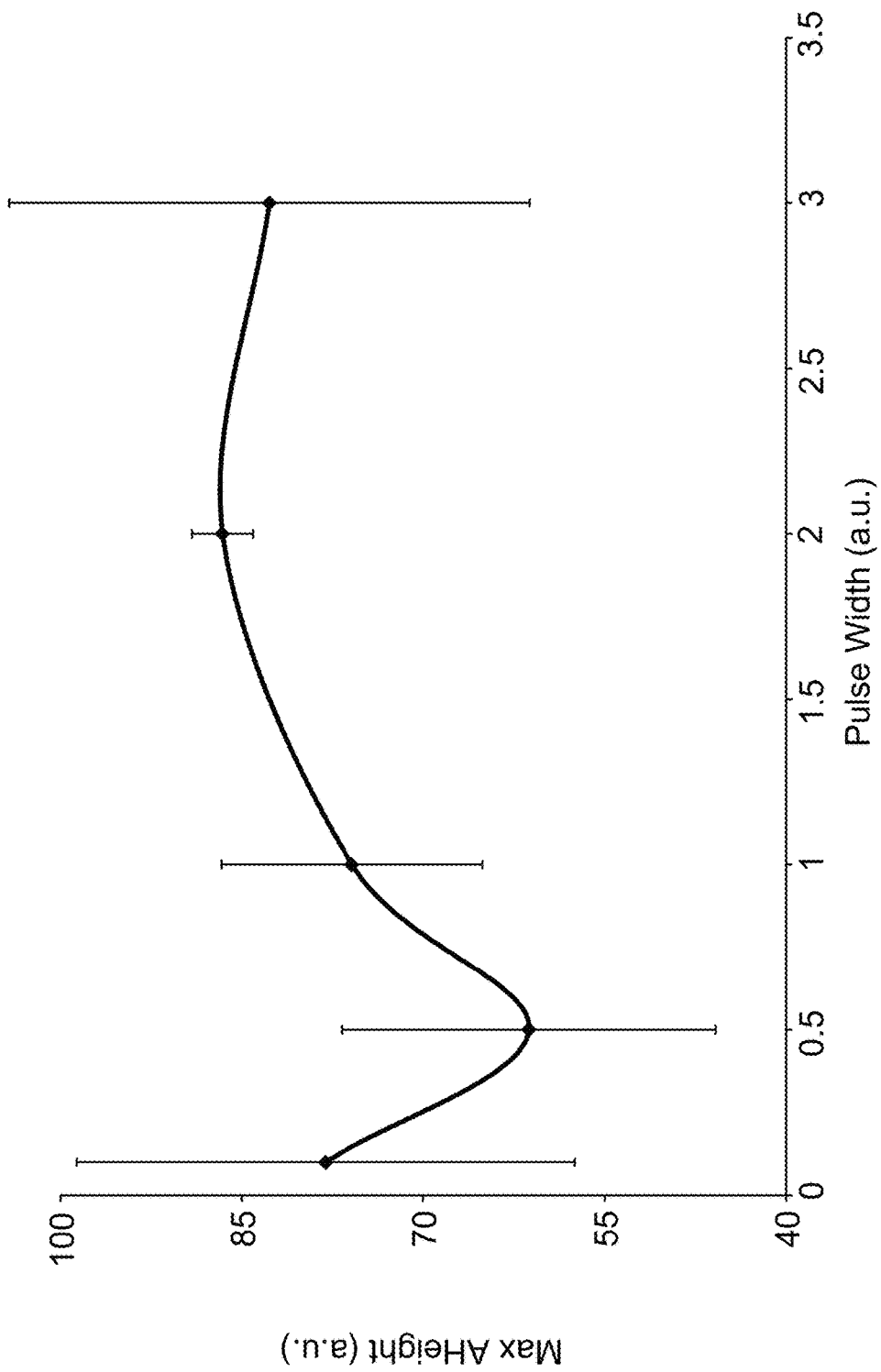
FIG. 8 is an exemplary graph depicting a substance of interest with a clustering agent as a function of pulse width in accordance with the present disclosure.

Example 4 is an exemplary embodiment of the effect of introducing the clustering agent (oxalic acid) in a pulsed manner. Specifically, as shown in FIG. 8, the pulse width indicates how long the desorber gate entrance was open for the clustering agent to enter into the desorber and react with the substance of interest. Example 4 indicates that when oxalic acid was introduced in a pulsed manner, the detector still detected the presence of sodium nitrate. Further, FIG. 8 shows the optimal pulse width of the example. That is, if the pulse was too short, not enough clustering agent was introduced, whereas if the pulse was too long, it was more difficult to resolve the sodium nitrate peak from the background of the detector.

Example 5

Figure 9:
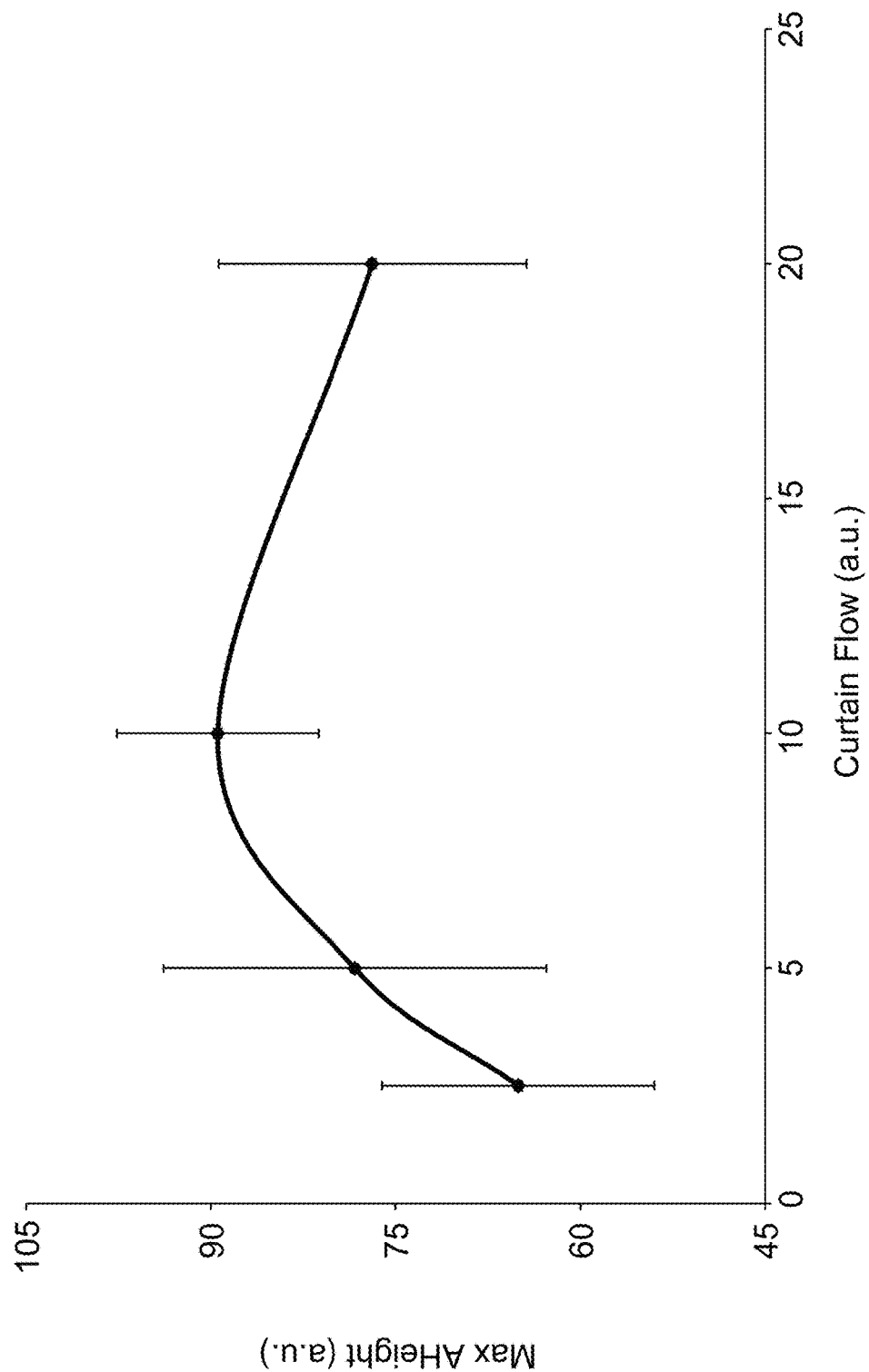
FIG. 9 is an exemplary graph depicting a substance of interest with a clustering agent as a function of curtain flow in accordance with the present disclosure.
Figure 10:
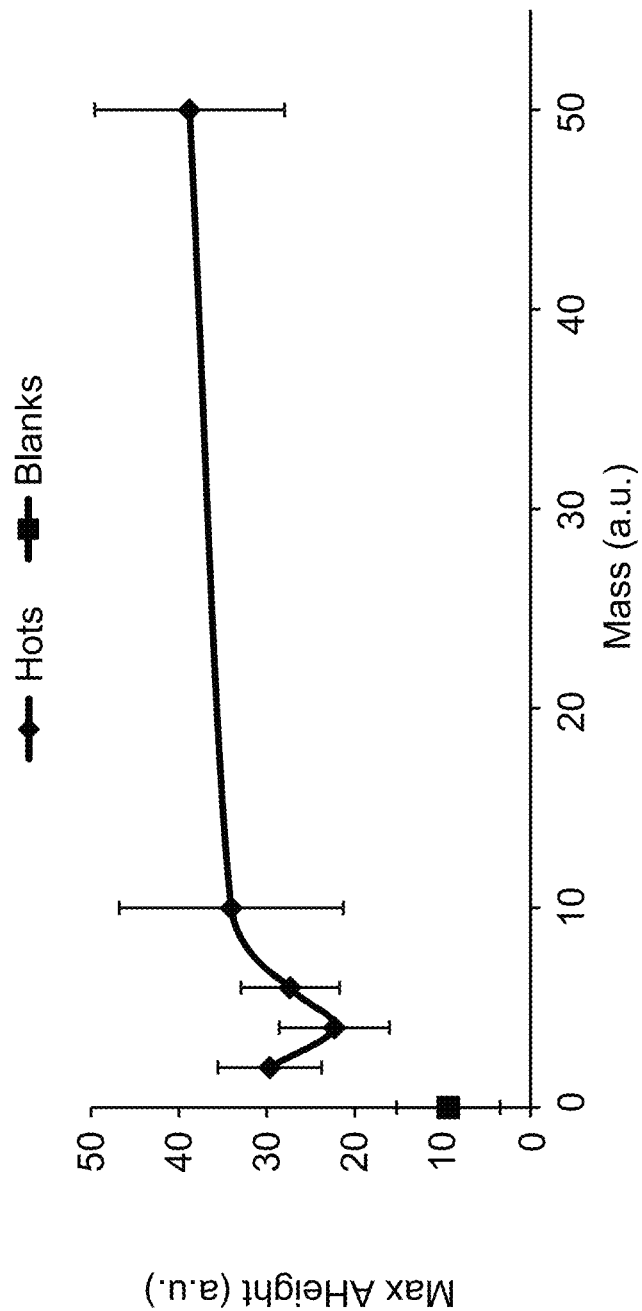
FIG. 10 is an exemplary graph comparing a constant flow of clustering agent and an increase in the amount of a substance of interest in accordance with the present disclosure.
Figure 11:
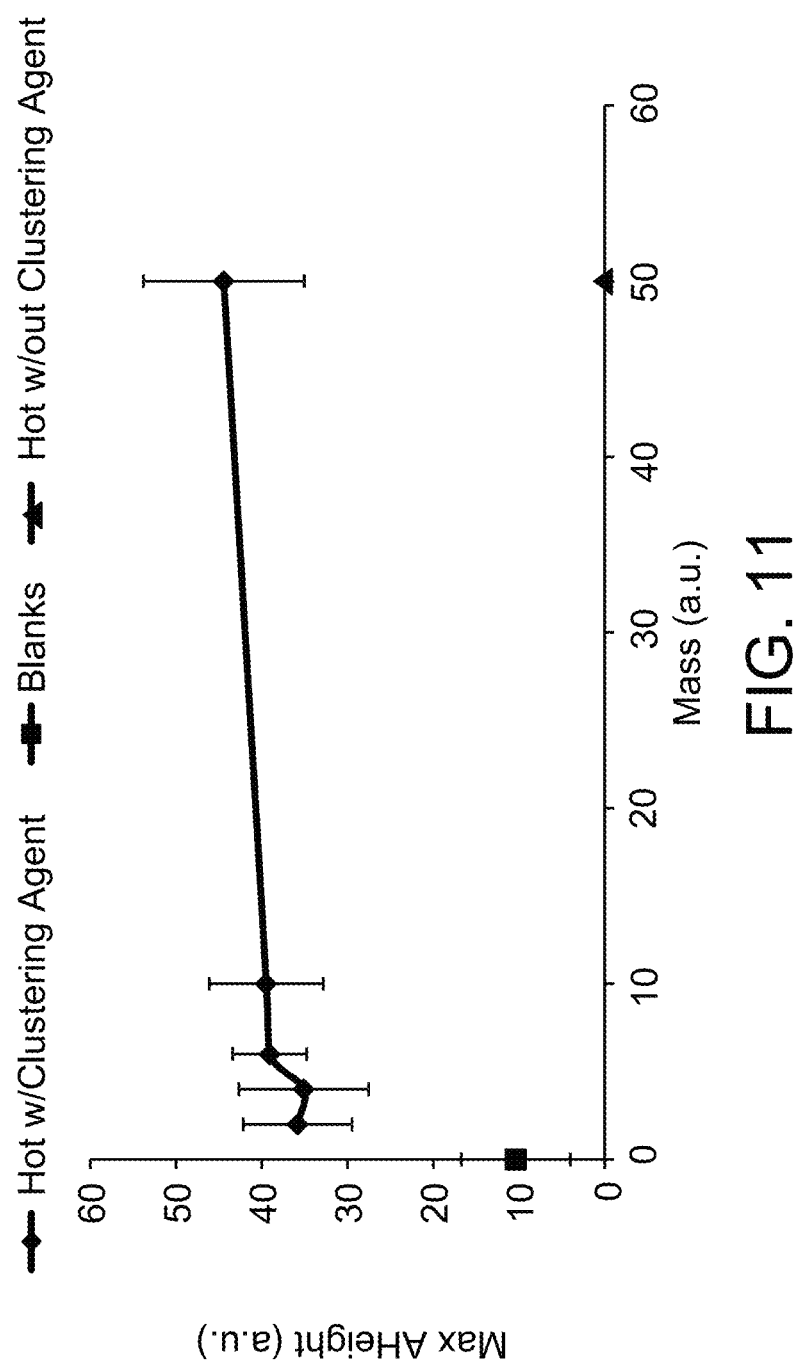
FIG. 11 is an exemplary graph comparing substance of interest detection with a clustering agent, without a clustering agent and without a substance of interest.

Example 5 is an exemplary embodiment of the effect of the curtain flow rate on the detection of sodium nitrate with oxalic acid used as the clustering agent. Specifically, as seen in FIG. 9, if the curtain flow rate becomes too high, then the clustering agent begins to get pushed out of the desorber and into the detector without having the time to interact with the sodium nitrate; conversely, if the flow rate was too low, an insufficient amount of clustering agent reached the detector. In such cases, the sodium nitrate was not vaporized and therefore ultimately not detected in the detector. As such, FIG. 9 indicates that the proper amount of curtain flow rate must be used in order to detect a substance of interest.

Example 6

Example 6 is an exemplary embodiment of the effect of a constant amount of clustering agent (oxalic acid) and an increasing amount of substance of interest (potassium nitrate) over time. Specifically, as shown in FIG. 10, when the amount of potassium nitrate was increased in the desorber and the amount of oxalic acid remained constant, the detector was still able to respond to the presence of potassium nitrate. Thus, Example 6 shows that oxalic acid chemically and/or physically modified the potassium nitrate such that the potassium nitrate was vaporized, transferred to the detector, and identified.

Example 7

Example 7 is an exemplary embodiment of the effect of a constant amount of clustering agent (oxalic acid) and an increasing amount of substance of interest (sodium chlorate) over time. Specifically, as shown in FIG. 11, when the amount of sodium chlorate was increased in the desorber and the amount of oxalic acid remained constant, the detector was still able to respond to the presence of sodium chlorate. Thus, Example 7 shows that oxalic acid chemically and/or physically modified the sodium chlorate such that the sodium chlorate was vaporized, transferred to the detector, and identified.

Further, as shown in Example 7 (FIG. 11), when the oxalic acid was not introduced into the desorber, the sodium chlorate was not detected, as identified by the triangle on the graph. Additionally, the square symbol on the graph represents the trial run when oxalic acid was present but sodium chlorate was not (i.e., system blank).

Example 8

Figure 12A:
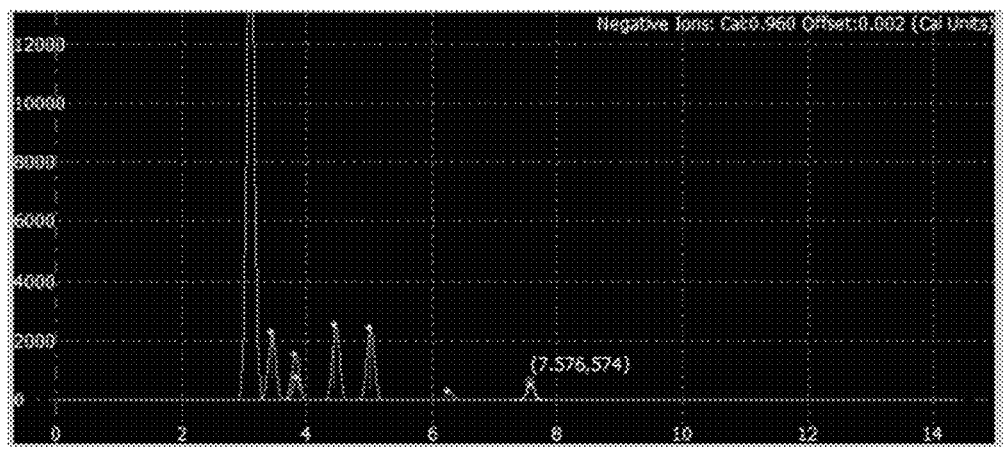
FIG. 12A is an exemplary graph depicting the ion mobility spectrum from a sampling medium without a substance of interest but with a continuous supply of a clustering agent in accordance with the present disclosure.

Example 8 is an exemplary embodiment of the effect of both a continuous and pulsed introduction of oxalic acid to the desorber, wherein the desorber included a trap containing sodium chlorate. Specifically, as shown in FIG. 12A, when the oxalic acid was supplied continuously but no sodium chlorate was present on the trap, then no peaks were detected. As shown in FIG. 12D, when sodium chlorate was present on the trap in the desorber but no oxalic acid was introduced into the desorber, then sodium chlorate was not detected by the detector when the substance of interest was transferred into the detector.

Figure 12B:
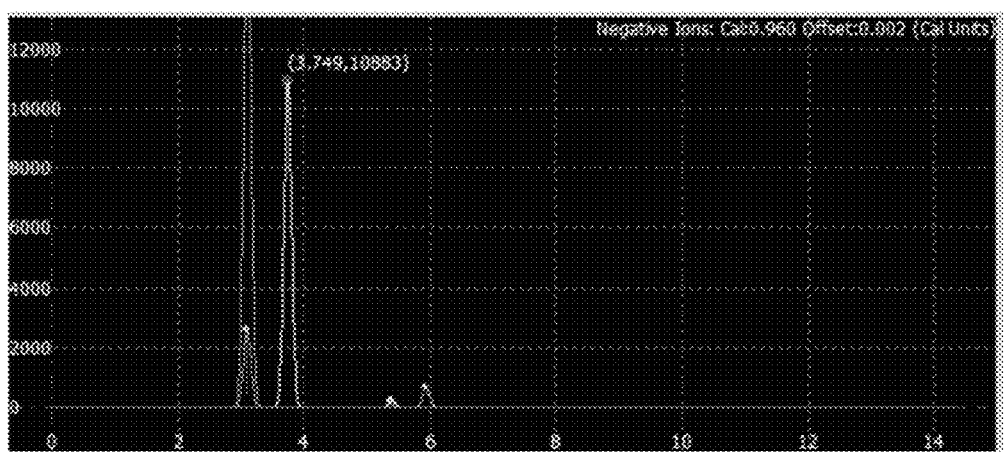
FIG. 12 B is an exemplary graph depicting the ion mobility spectrum of a substance of interest and a continuous supply of a clustering agent in accordance with the present disclosure.
FIG. 12C is an exemplary graph depicting the ion mobility spectrum of a substance of interest and a pulsed supply of a clustering agent in accordance with the present disclosure.
FIG. 12D is an exemplary graph depicting the ion mobility spectrum from a sampling medium containing a substance of interest but without a clustering agent in accordance with the present disclosure.
Figure 12C:
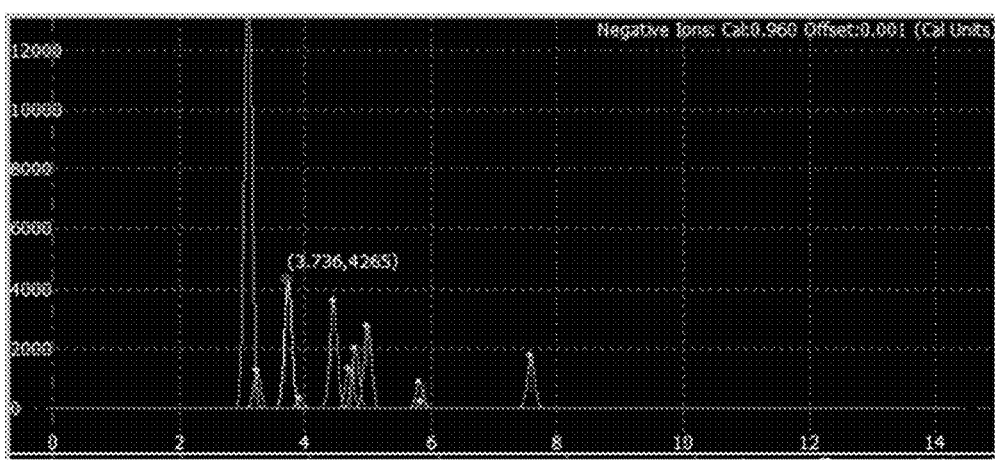
Figure 12D:
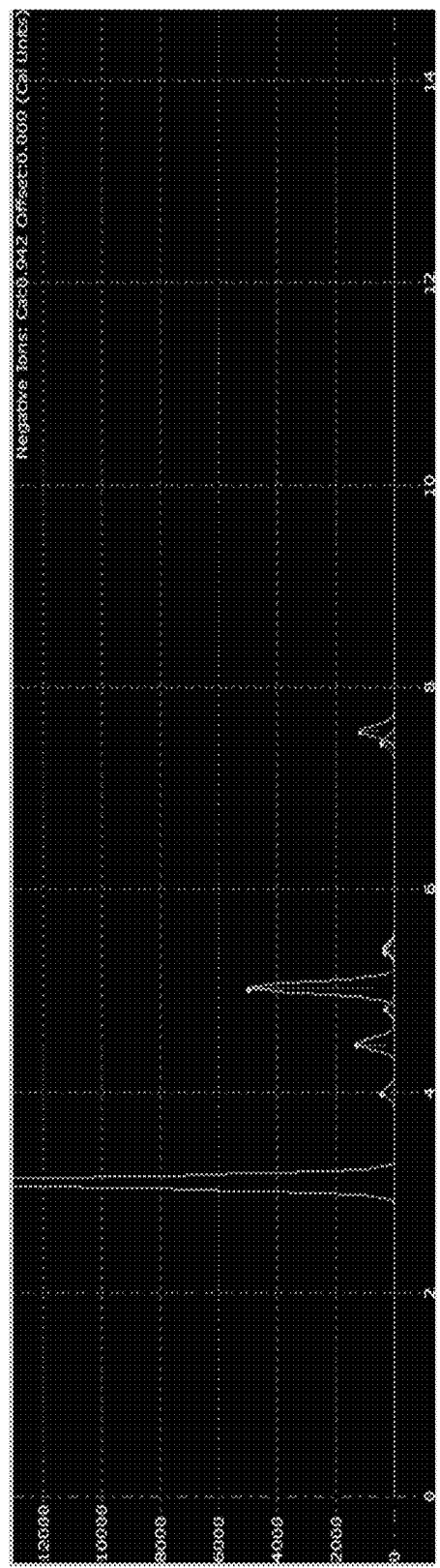

As shown in FIG. 12B, however, when sodium chlorate was present on the trap in the desorber and oxalic acid was continuously supplied to the desorber, then sodium chlorate was detected when the substance of interest was transferred into the detector corresponding to a drift time of about 3.7 calibrated units. Additionally, as shown in FIG. 12C, the sodium chlorate peak of about 3.7 calibrated units was also detected when sodium chlorate was present on the trap in the desorber and oxalic acid was supplied in a pulsed manner to the desorber. As such, Example 8 proved that whether supplied continuously or in a pulsed manner, oxalic acid was effective at modifying the sodium chlorate such that the sodium chlorate was detected in the detector.

Example 9

Figure 13:
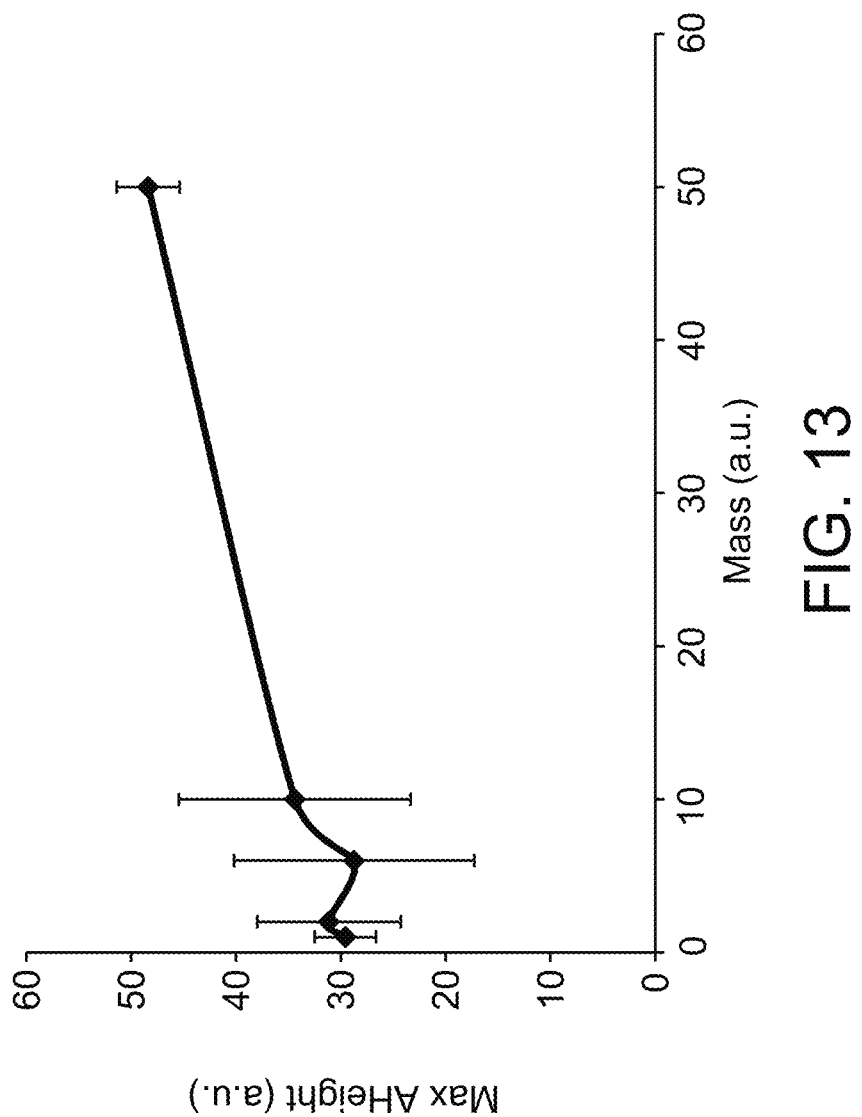
FIG. 13 is an exemplary graph comparing a constant flow of clustering agent and an increase in the amount of a substance of interest in accordance with the present disclosure.

Example 9 is an exemplary embodiment of the effect of a constant amount of clustering agent (lactic acid) and an increasing amount of substance of interest (sodium nitrate) over time. Specifically, as shown in FIG. 13, when the amount of sodium nitrate was increased in the desorber and the amount of lactic acid remained constant, the detector was still able to respond to the presence of sodium nitrate. Thus, Example 9 shows that lactic acid chemically and/or physically modified the sodium nitrate such that the sodium nitrate was vaporized, transferred to the detector, and identified.

Exemplary embodiments of substance detection systems for determining the presence of substances of interest, and methods of operating such systems are not limited to the specific embodiments described herein, but rather, components of systems and/or steps of the methods may be utilized independently and separately from other components and/or steps described herein. For example, the methods may also be used in combination with other systems requiring determining the presence of substances of interest, and are not limited to practice with only the substance detection systems and methods as described herein. Rather, the exemplary embodiment can be implemented and utilized in connection with many other substance detection applications that are currently configured to determine the presence of substances of interest.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting a substance of interest using a detection system comprising a pump, a first housing, and a second housing containing a condensed version of a vaporized clustering agent, the method comprising:
   collecting a sample of a substantially non-volatile substance of interest on a sampling trap;
   inserting the trap into a thermal desorber wherein the thermal desorber comprises the first housing;
   generating the vaporized clustering agent by pumping air, using the pump, into the second housing through a cartridge comprising sieves and subjecting the condensed version of the vaporized clustering agent in the second housing to at least one of corona discharge, laser ablation, current-induced desorption, a heating block, or combinations thereof;
   introducing the vaporized clustering agent into the desorber, wherein the clustering agent increases the volatility of the substance of interest and wherein the vaporized clustering agent is introduced into the desorber by transferring the vaporized clustering agent from the second housing into the first housing through a transfer line;
   vaporizing the substance of interest;
- transferring the vaporized substance of interest into a detector;
- performing an analysis of the substance of interest; and,
- detecting the substance of interest.

2. The method of claim 1, wherein the vaporized clustering agent includes at least one of an organic acid, a crown ether, an amine, an ester, an amide or combinations thereof.

3. The method of claim 1, wherein the substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant or combinations thereof.

4. The method of claim 3, wherein the substance of interest includes at least one of nitrates, chlorates, perchlorates, nitrites, chlorites, permanganates, chromates, dichromates, bromates, iodates, or combinations thereof.

5. The method of claim 1, wherein the vaporized clustering agent is introduced into the desorber at a flow rate of from about 5 cc/min to about 1,000 cc/min.

6. The method of claim 1, wherein the vaporized clustering agent is introduced into the desorber at a concentration of from about 0.01 µg/min to about 250 µg/min.

7. The method of claim 1, wherein the detector includes at least one of an ion mobility spectrometer (IMS), an ion trap mobility spectrometer (ITMS), a drift spectrometer (DS), an aspiration ion mobility spectrometer, a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS), a differential mobility spectrometer (DMS), a drift spectrometer, a non-linear drift spectrometer, an ultra-high FAIMS, a trapped ion mobility spectrometer (TIMS), a traveling wave ion mobility spectrometer, a semiconductor gas sensor, a raman spectrometer, a laser diode detector, a mass spectrometer (MS), a gas chromatograph (GC), an electron capture detector, a photoionization detector, a chemiluminescence-based detector, an electrochemical sensor, an infrared spectrometer, a lab-on-a-chip detector or combinations thereof.

8. The method of claim 1, wherein the vaporized clustering agent is applied in a pulsed manner.

9. The method of claim 1, wherein the vaporized clustering agent is applied in a pulsed manner using at least one of a pulse rate in a range from 0.01 Hz to 10,000 Hz or a pulse width in a range of 1 second to 10 seconds.

10. The method of claim 1, wherein the vaporized clustering agent is applied in a pulsed manner using at least one of a pulse rate in a range from 0.01 Hz to 100 Hz or a pulse width in a range of 3 seconds to 7 seconds.

11. The method of claim 1, wherein the vaporized clustering agent includes at least one of an organic acid, a crown ether, an amine, an ester, an amide or combinations thereof.

12. The method of claim 1 wherein generating the vaporized clustering agent comprises containing the clustering agent in both its condensed and vaporized form within a permeation tube configured in the second housing.

13. A method for detecting a substance of interest using a detection system comprising a pump, a thermal desorber comprising a first housing, and a second housing, separate from the first housing, containing a condensed version of a vaporized clustering agent, the method comprising:

pumping dry air into the second housing using the pump;
subjecting the condensed version of the vaporized clustering agent in the second housing to at least one of corona discharge, laser ablation, current-induced desorption, a heating block, or combinations thereof to generate the vaporized clustering agent;
introducing the vaporized clustering agent into the desorber by transferring the vaporized clustering agent from the second housing into the first housing through a transfer line;
increasing the volatility of a substantially non-volatile substance of interest, wherein the volatility of the substance of interest is increased by applying the vaporized clustering agent to the substance of interest;
vaporizing the substance of interest in the thermal desorber; and,
transferring the vaporized substance of interest into a detector, wherein the detector performs an analysis of the vaporized substance of interest and detects the substance of interest.

14. The method of claim 13, wherein the vaporized clustering agent includes at least one of an organic acid, a crown ether, an amine, an ester, an amide or combinations thereof.

15. The method of claim 13, wherein the substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant or combinations thereof.

16. The method of claim 15, wherein the substance of interest includes at least one of nitrates, chlorates, perchlorates, nitrites, chlorites, permanganates, chromates, dichromates, bromates, iodates, or combinations thereof.

17. The method of claim 13, wherein the vaporized clustering agent is applied at a flow rate of from about 5 cc/min to about 1,000 cc/min.

18. The method of claim 13, wherein the vaporized clustering agent is applied at a concentration of from about 0.01 µg/min to about 250 µg/min.

19. The method of claim 13, wherein the detector includes at least one of an ion mobility spectrometer (IMS), an ion trap mobility spectrometer (ITMS), a drift spectrometer (DS), an aspiration ion mobility spectrometer, a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS), a differential mobility spectrometer (DMS), a drift spectrometer, a non-linear drift spectrometer, an ultra-high FAIMS, a trapped ion mobility spectrometer (TIMS), a traveling wave ion mobility spectrometer, a semiconductor gas sensor, a raman spectrometer, a laser diode detector, a mass spectrometer (MS), a gas chromatograph (GC), an electron capture detector, a photoionization detector, a chemiluminescence-based detector, an electrochemical sensor, an infrared spectrometer, a lab-on-a-chip detector or combinations thereof.

20. The method of claim 13, wherein the vaporized clustering agent is applied in a pulsed manner.

21. The method of claim 13, wherein the vaporized clustering agent is applied in a pulsed manner using at least one of a pulse rate in a range from 0.01 Hz to 10,000 Hz or a pulse width in a range of 1 second to 10 seconds.

22. The method of claim 13, wherein the vaporized clustering agent is applied in a pulsed manner using at least one of a pulse rate in a range from 0.01 Hz to 100 Hz or a pulse width in a range of 3 seconds to 7 seconds.

* * * * *